United States Patent [19]

Clark, III

[11] 4,020,847

[45] May 3, 1977

[54] ROTATING CUTTER CATHETER

[76] Inventor: William T. Clark, III, 6 Davis Blvd., New Orleans, La. 70121

[22] Filed: Nov. 5, 1975

[21] Appl. No.: 628,980

[52] U.S. Cl. .................................. 128/305; 128/2 B
[51] Int. Cl.² ........................................ A61B 17/32
[58] Field of Search .......... 128/2 B, 276, 305, 304, 128/311, 347; 27/24 A

[56] References Cited

UNITED STATES PATENTS

| 1,585,934 | 5/1926 | Muir | 128/2 B |
| 1,663,761 | 3/1928 | Johnson | 128/2 B |
| 2,437,329 | 3/1948 | Moore | 128/2 B |
| 2,495,794 | 1/1950 | Weller | 128/2 B |
| 2,729,210 | 1/1956 | Spencer | 128/2 B |
| 2,739,585 | 3/1956 | Ayre | 128/2 B |
| 3,088,454 | 5/1963 | Shute | 128/2 B |
| 3,230,949 | 1/1966 | Rodriquez-Olleros | 128/305 X |
| 3,730,185 | 5/1973 | Cook et al. | 128/304 X |

FOREIGN PATENTS OR APPLICATIONS

| 177,011 | 12/1953 | Austria | 128/304 |

Primary Examiner—Channing L. Pace

[57] ABSTRACT

An elongate blunt-ended hollow tube is affixed on the distal end of a flexible catheter. A cutting edge along one side of a lengthwise slot in the tube wall cuts off irregularities from the inside of a vessel and feeds them into the hollow interior of the tube as the catheter is rotated.

2 Claims, 3 Drawing Figures

ROTATING CUTTER CATHETER

FIELD OF INVENTION

Surgery, Cannula, Catheter.

OBJECTS

The object of this invention is to provide a means of capturing and removing clot-forming irregularities on the intima of the human vascular system. Such irregularities are resistant to surgical correction and may so profoundly after the dynamics of blood flow that clotting is precipitated.

Irregularities on the vascular intima may take many forms, and they may be firmly or loosely attached. Loosely-attached irregularities are particularly troublesome because they may form "flaps" and "strings" which intermittently affect blood flow but, because they are loosely attached, they are mobile, and therefore resistant to removal by conventional balloon catheterization. The present invention can remove such irregularities because it captures them and cuts them loose from the intima.

More specifically, it is intended now to provide a flexible catheter to the distal end of which is attached a hollow tube closed at the end with a rounded point. In the wall of the tube are one or more cutting edges or teeth which are cut on the side as the tube is rotated in the vessel. The edges are ground so that they cut in only one direction of rotation.

These and other objects will be apparent from the following specification and drawings, in which.

Figure 1:
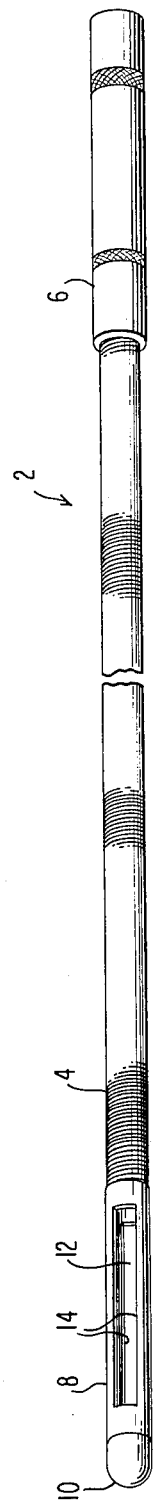
FIG. 1 is a plan view of the catheter.
Figure 2:
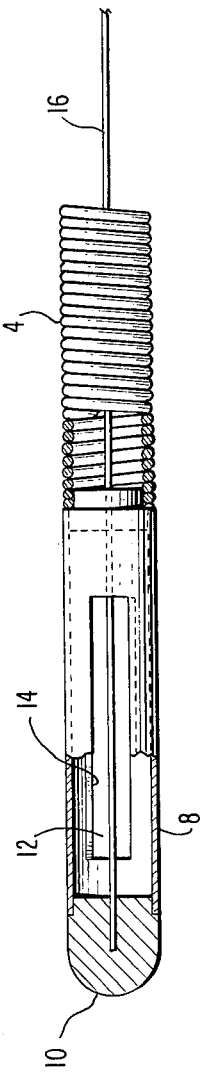
FIG. 2 is an enlarged view partly broken away of the distal end of the catheter; and, FIG. 3 is a plan view of the distal end of the catheter, with a modified form of cutting edge.

Referring now to FIGS. 1 and 2 of the drawing, the catheter 2 consists of an elongate flexible shaft 4, preferably made of a helically wound stainless steel spring having a handle 6 on one end. To the other end of shaft 4 is attached an elongate hollow tube 8 having a rounded, blunt end 10 and a pair of elongate slots 12 running lengthwise through the tube wall. Knife edges 14 extend along corresponding sides of the slots. If desired, a flexible wire running through flexible shaft 4 and tube 8, and having one end attached to handle 6 and the other end attached to the blunt end 10 of tube 8, may be provided to ensure that the tube will not come loose from the end of the flexible shaft.

Figure 3:
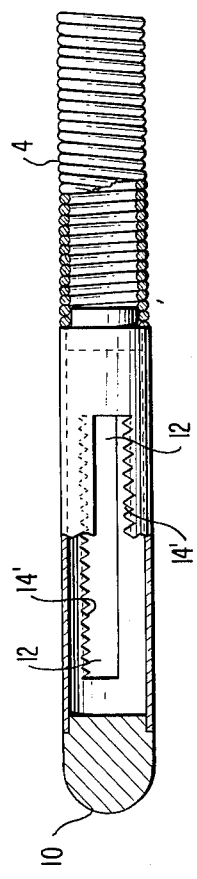

The catheter shown in FIG. 3 is the same as the one shown in FIGS. 1 and 2, except in that the knife edges 14' are serrated to enhance its capturing capabilities. Different types of cutting edges can be used, the ones shown being merely illustrative. Also, one, two or more slots with cutting edges may be provided.

In use, the catheter is introduced into the affected vessel and rotated in the cutting direction as necessary as it is pushed along. When the vessel is cleared, the instrument is withdrawn with the incised material or debris held in the hollow of the tube. The instrument may be rotated in the opposite direction to facilitate removal and minimize the possibility of unintentional cutting. It is important to note that no cutting edge protrudes beyond the outside diameter of the tube. This minimizes the risk of vessel injury. The slotted tube may be conveniently made of hard-drawn stainlesssteel or other tissue-inert, radiopaque, sterilizable material which will hold an edge. The tube must be firmly attached in use, but may be replaceable.

I claim:

1. A catheter comprising
   a flexible shaft,
   an elongate hollow tube formed by a concavo-convex wall having one end attached to said shaft and the other end being blunt,
   said tube having at least one lengthwise slot in the wall thereof and a cutting edge along one side of said slot,
   said tube being of circular cross-section, said cutting edge being disposed not outside of the circle of the tube cross section and being an edge of the tube wall.

2. A catheter as claimed in claim 1, said cutting edge being serrated.